(12) United States Patent
Lee et al.

(10) Patent No.: US 11,742,521 B2
(45) Date of Patent: Aug. 29, 2023

(54) ELECTROLYTE SOLUTION FOR LITHIUM SECONDARY BATTERY AND LITHIUM SECONDARY BATTERY COMPRISING SAME

(71) Applicants: HYUNDAI MOTOR COMPANY, Seoul (KR); KIA CORPORATION, Seoul (KR); UNIST (ULSAN NATIONAL INSTITUTE OF SCIENCE AND TECHNOLOGY), Ulsan (KR)

(72) Inventors: Yoon Sung Lee, Suwon-si (KR); Seung Min Oh, Incheon (KR); Sung Ho Ban, Hwaseong-si (KR); Ko Eun Kim, Cheongju-si (KR); Jun Ki Rhee, Suwon-si (KR); Woo Young Jin, Busan (KR); Sang Kyu Kwak, Ulsan (KR); Nam Soon Choi, Ulsan (KR); Sung You Hong, Ulsan (KR); Woo Gyum Kim, Ulsan (KR); Dae Yeon Hwang, Ulsan (KR); Hyeon Gyu Moon, Hwaseong-si (KR)

(73) Assignees: HYUNDAI MOTOR COMPANY, Seoul (KR); KIA CORPORATION, Seoul (KR); UNIST (ULSAN NATIONAL INSTITUTE OF SCIENCE AND TECHNOLOGY), Ulsan (KR)

(*) Notice: Subject to any disclaimer, the term of this patent is extended or adjusted under 35 U.S.C. 154(b) by 252 days.

(21) Appl. No.: 17/338,244

(22) Filed: Jun. 3, 2021

(65) Prior Publication Data
US 2022/0131190 A1 Apr. 28, 2022

(30) Foreign Application Priority Data
Oct. 28, 2020 (KR) .................. 10-2020-0141277

(51) Int. Cl.
| $H01M$ $10/0567$ | (2010.01) |
| $H01M$ $10/0525$ | (2010.01) |
| $H01M$ $10/0569$ | (2010.01) |
| $C07D$ $249/06$ | (2006.01) |
| $H01M$ $10/0568$ | (2010.01) |

(52) U.S. Cl.
CPC ...... *H01M 10/0567* (2013.01); *C07D 249/06* (2013.01); *H01M 10/0525* (2013.01); *H01M 10/0568* (2013.01); *H01M 10/0569* (2013.01); *H01M 2300/0025* (2013.01)

(58) Field of Classification Search
None
See application file for complete search history.

(56) References Cited

FOREIGN PATENT DOCUMENTS
KR 10-1264435 5/2013

*Primary Examiner* — Eli S Mekhlin
(74) *Attorney, Agent, or Firm* — Lempia Summerfield Katz LLC

(57) ABSTRACT

The electrolyte solution for a lithium secondary battery includes: a lithium salt; a solvent; and an anode additive
(Continued)

Figure 1:
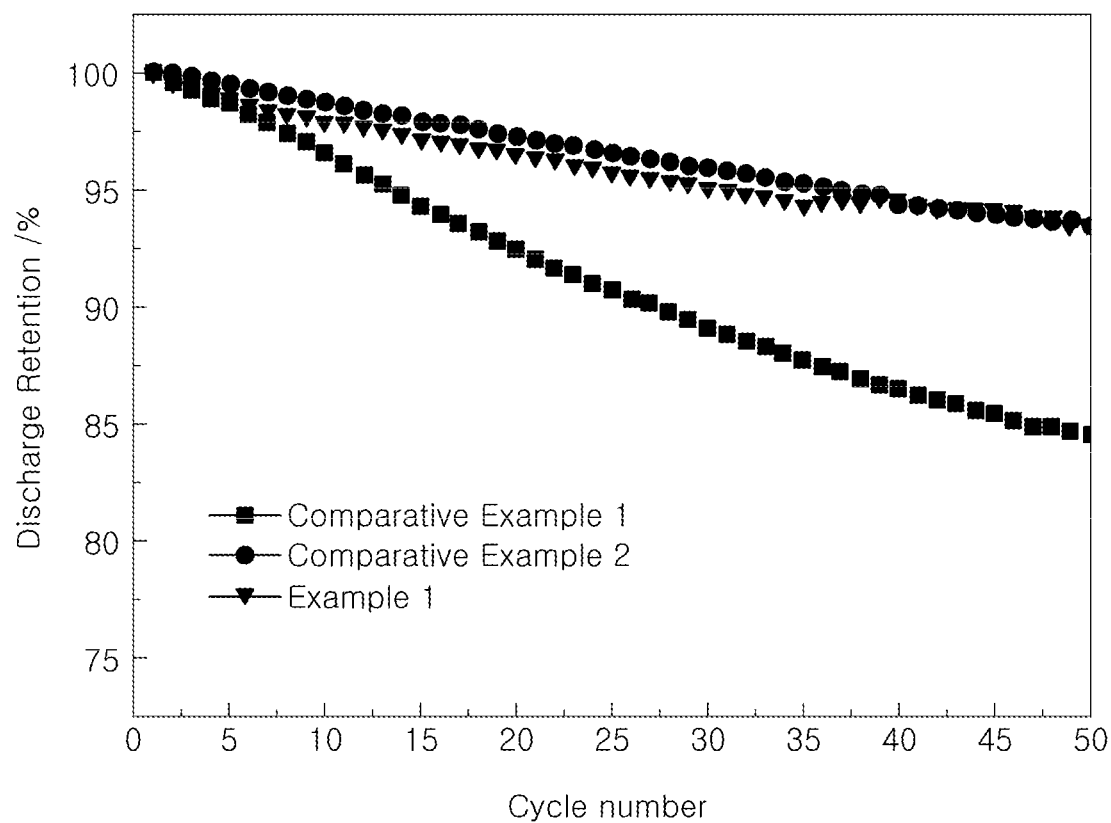

including 5-(4-cyanophenyl)-1-(4-fluorobenzyl)-1H-1,2,3-triazole-4-carbonitrile represented by Chemical Formula 1 below:
[Chemical Formula 1]
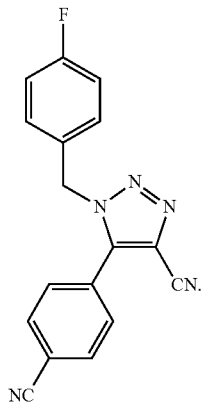
9 Claims, 2 Drawing Sheets

ELECTROLYTE SOLUTION FOR LITHIUM SECONDARY BATTERY AND LITHIUM SECONDARY BATTERY COMPRISING SAME

CROSS REFERENCE TO RELATED APPLICATION

The present application claims priority to and the benefit of Korean Patent Application No. 10-2020-0141277, filed on Oct. 28, 2020, the entire content of which are incorporated herein by reference.

FIELD

The present disclosure relates to an electrolyte solution for a lithium secondary battery and a lithium secondary battery including the same.

BACKGROUND

The statements in this section merely provide background information related to the present disclosure and may not constitute prior art.

A lithium secondary battery is used as a power source for smartphones, laptop computers, hybrid vehicles and electric vehicles. The lithium secondary battery is rechargeable and is advantageous because of the high energy density, high power output, and high charging speed thereof compared to conventional lead-acid batteries, nickel/metal-hydride batteries, and the like.

A lithium secondary battery is configured to include a cathode that provides lithium during charging, an anode that receives lithium, an electrolyte, which is a passage for lithium ions to move, and a separator, which inhibits contact between the cathode and the anode. A lithium secondary battery generates electrical energy using a change in chemical potential when lithium ions stored in the anode are deintercalated and are intercalated at the cathode.

When the lithium secondary battery is repeatedly charged and discharged, the structures of the cathode and the anode become different from the initial state thereof depending on the intercalation/deintercalation of lithium ions, and the capacity and power output of the battery decrease. Therefore, protecting the cathode and the anode to increase the lifetime of the battery and to inhibit a decrease in power output is a major challenge facing the industry.

During initial charging of a lithium secondary battery, an irreversible reaction in which electric charges are used in excess between the anode/cathode and the electrolyte solution proceeds. By the irreversible reaction, a solid electrolyte interface (SEI) is formed on the surface of the anode, and a cathode protective film is formed on the surface of the cathode. These films serve as a tunnel for lithium ions, and simultaneously serve to inhibit deformation of anode and cathode active materials and to inhibit decomposition of the electrolyte solution during charging and discharging.

Therefore, when the SEI and the cathode protective film, having high stability and low resistance, are formed, the lifetime of the lithium secondary battery may be increased and a decrease in power output may be inhibited.

Details set forth as the background art are provided for the purpose of better understanding the background of the disclosure, and are not to be taken as an admission that the described details correspond to the conventional technology already known to those skilled in the art.

SUMMARY

The present disclosure provides an electrolyte solution for a lithium secondary battery capable of increasing the lifetime of a lithium secondary battery and a lithium secondary battery including the same.

One form of the present disclosure provides an electrolyte solution for a lithium secondary battery including a lithium salt, a solvent, and an additive, in which the additive includes 5-(4-cyanophenyl)-1-(4-fluorobenzyl)-1H-1,2,3-triazole-4-carbonitrile represented by Chemical Formula 1 below:

[Chemical Formula 1]

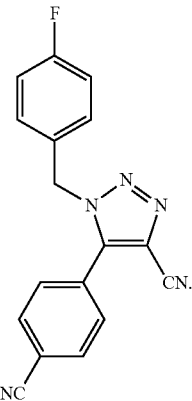

The amount of the compound represented by Chemical Formula 1 may be 0.5 wt % to 1.5 wt % based on the total weight of the electrolyte solution.

The electrolyte solution may further include, as the additive, vinyl chloride (VC) in an amount of 0.5 wt % to 3.0 wt % based on the total weight of the electrolyte solution.

The lithium salt may be any one compound or a mixture of two or more selected compounds from the group consisting of $LiPF_6$, $LiBF_4$, $LiClO_4$, $LiCl$, $LiBr$, $LiI$, $LiB_{10}Cl_{10}$, $LiCF_3SO_3$, $LiCF_3CO_2$, $LiAsF_6$, $LiSbF_6$, $LiAlCl_4$, $CH_3SO_3Li$, $CF_3SO_3Li$, $LiN(SO_2C_2F_5)_2$, $Li(CF_3SO_2)_2N$, $LiC_4F_9SO_3$, $LiB(C_6H_5)_4$, $Li(SO_2F)_2N(LiFSI)$, and $(CF_3SO_2)_2NLi$.

The solvent may be any one substance or a mixture of two or more substances selected from the group consisting of a carbonate-based solvent, an ester-based solvent, an ether-based solvent, and a ketone-based solvent.

Another form of the present disclosure provides a lithium secondary battery including the electrolyte solution described above, a cathode including a cathode active material containing Ni, Co and Mn, an anode including a carbon (C)-based anode active material, and a separator interposed between the cathode and the anode.

The lithium secondary battery may exhibit a discharge retention of 84.6% or more after 50 cycles under conditions of a discharge end voltage of 2.5 V, a charge end voltage of 4.2 V, a temperature of 45° C. during charging and discharging, and a C-rate of 1C.

According to the present disclosure, an additive that forms a CEI (cathode electrolyte interface) on a cathode and an SEI (solid electrolyte interface) on an anode is added to an electrolyte solution, thereby increasing the high-temperature lifetime of a lithium secondary battery.

Further areas of applicability will become apparent from the description provided herein. It should be understood that the description and specific examples are intended for purposes of illustration only and are not intended to limit the scope of the present disclosure.

DRAWINGS

Figure 2:
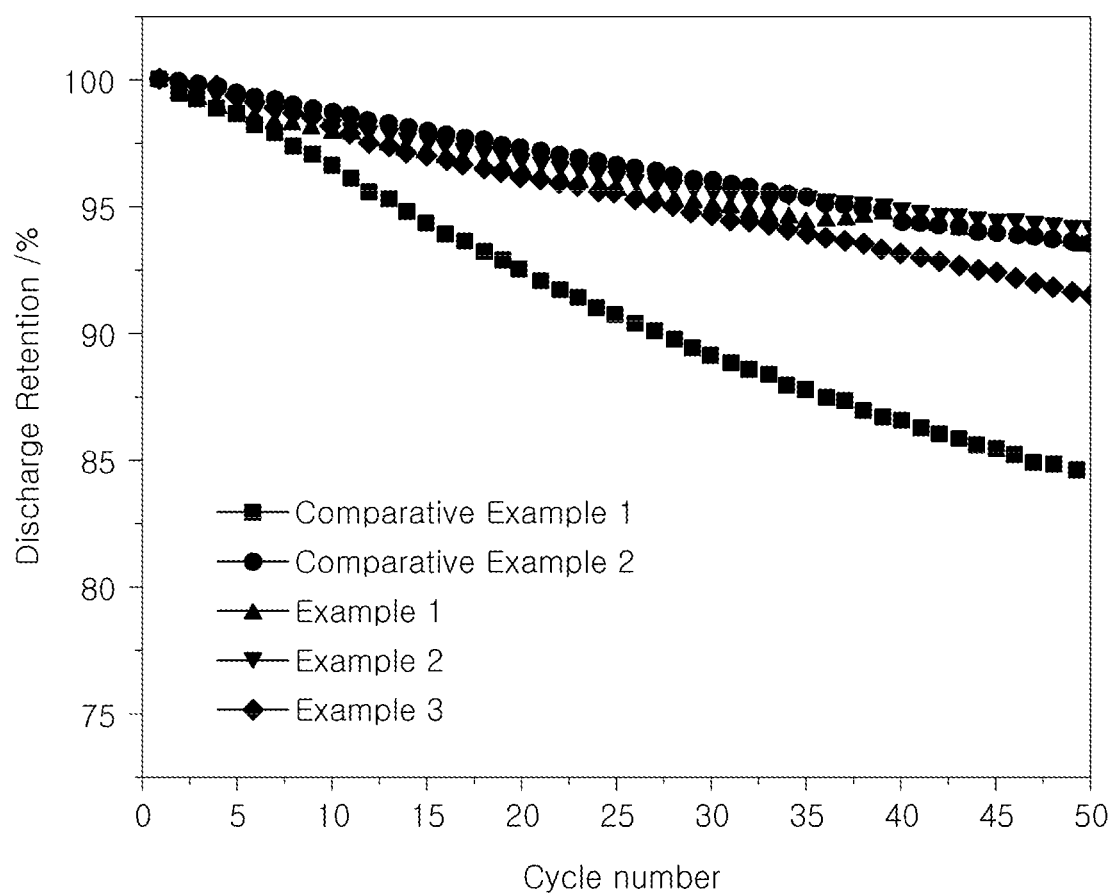

In order that the disclosure may be well understood, there will now be described various forms thereof, given by way of example, reference being made to the accompanying drawings, in which:

FIGS. 1 and 2 are graphs showing the results of measurement of properties depending on the presence of an additive in Examples according to the present disclosure and Comparative Examples.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Hereinafter, a detailed description will be given of various forms of the present disclosure with reference to the appended drawings. However, the present disclosure is not limited to the following forms, and may be changed to have a variety of different forms. These forms are provided to complete the disclosure of the present disclosure and to fully describe the present disclosure to those skilled in the art.

According to one form of the present disclosure, an electrolyte solution for a lithium secondary battery is a material for forming an electrolyte that is applied to a lithium secondary battery, and includes a lithium salt, a solvent, and an anode additive.

The lithium salt may be any one compound or a mixture of two or more compounds selected from the group consisting of $LiPF_6$, $LiBF_4$, $LiClO_4$, LiCl, LiBr, LiI, $LiB_{10}Cl_{10}$, $LiCF_3SO_3$, $LiCF_3CO_2$, $LiAsF_6$, $LiSbF_6$, $LiAlCl_4$, $CH_3SO_3Li$, $CF_3SO_3Li$, $LiN(SO_2C_2F_5)_2$, $Li(CF_3SO_2)_2N$, $LiC_4F_9SO_3$, $LiB(C_6H_5)_4$, $Li(SO_2F)_2N(LiFSI)$, and $(CF_3SO_2)_2NLi$.

The solvent may be any one substance or a mixture of two or more substances selected from the group consisting of a carbonate-based solvent, an ester-based solvent, an ether-based solvent, and a ketone-based solvent.

Examples of the carbonate-based solvent may include, but are not limited to, dimethyl carbonate (DMC), diethyl carbonate (DEC), dipropyl carbonate (DPC), methyl propyl carbonate (MPC), ethyl propyl carbonate (EPC), ethyl methyl carbonate (EMC), ethylene carbonate (EC), propylene carbonate (PC), butylene carbonate (BC), fluoroethylene carbonate (FEC), vinylene carbonate (VC) and the like. Examples of the ester-based solvent may include, but are not limited to, γ-butyrolactone (GEL), n-methyl acetate, n-ethyl acetate, n-propyl acetate, and the like, and examples of the ether-based solvent may include, but are not limited to, dibutyl ether and the like.

The solvent may further include an aromatic hydrocarbon-based organic solvent. Specific examples of the aromatic hydrocarbon-based organic solvent include benzene, fluorobenzene, bromobenzene, chlorobenzene, cyclohexylbenzene, isopropylbenzene, n-butylbenzene, octylbenzene, toluene, xylene, mesitylene, and the like, which may be used alone or in combination.

Meanwhile, the additive that is added to the electrolyte solution according to one form of the present disclosure may include 5-(4-cyanophenyl)-1-(4-fluorobenzyl)-1H-1,2,3-triazole-4-carbonitrile, represented by Chemical Formula 1 below:

[Chemical Formula 1]

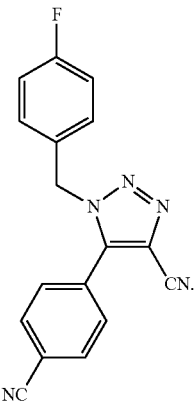

The additive serves to form an SEI (solid electrolyte interface) on the anode and a CEI (cathode electrolyte interface) on the cathode to thus increase the lifetime of a battery, and is preferably used in an amount of 1.5 wt % or less, and more preferably 0.5 to 1.0 wt %, based on the total weight of the electrolyte solution.

If the amount of the additive exceeds 1.5 wt %, the CEI and SEI films may be excessively formed, thus increasing cell resistance, which may deteriorate the power output of the cell. On the other hand, if the amount of the anode additive is less than 0.5 wt %, the CEI and SEI films may be insufficiently formed, which may drastically decrease the lifetime of the cell.

Specifically, when the additive contains a polar functional group or an unsaturated functional group such as a double bond or a triple bond at the terminal of the molecule thereof, it may exhibit strong capability to receive electrons from the anode compared to when a polar solvent is used, and thus may be reduced at a low voltage. Accordingly, the additive is capable of forming a bond through direct reaction with a carbon anode, forming a bond through reaction with a functional group present on the surface of the anode, or being adsorbed to the surface of the anode, resulting in formation of SEI on the surface of the anode.

In addition, when the additive contains a polar functional group such as a nitrile group, it may form a bond with a transition metal such as cobalt at the cathode, resulting in a complex structure.

It is confirmed for the additive represented by Chemical Formula 1 that the benzonitrile (cyanophenyl group) moiety is involved in the formation of SEI and the 1,2,3-triazole-4-carbonitrile moiety is involved in the formation of CEI.

The resulting SEI is formed on the anode and thus becomes a passage for lithium ions to move, inhibits a chemical reaction from occurring between the electrolyte solution and the electrode, and suppresses degeneration of the anode during charging and discharging, thereby improving the lifetime and high-temperature stability of the lithium secondary battery. The CEI is formed on the cathode to suppress the dissolution of transition metal ions (e.g. Ni, Co, Mn, etc.) for a cathode active material into the electrolyte solution, thereby inhibiting a rapid decrease in battery capacity and a decrease in battery lifetime. Moreover, it is possible to use transition metals that have not been conventionally used for the cathode active material due to dissolution.

In addition, a lithium secondary battery according to one form of the present disclosure is configured to include a cathode, an anode, and a separator, in addition to the electrolyte solution described above.

The cathode includes an NCM-based cathode active material containing Ni, Co and Mn. In particular, in the present form, the cathode active material included in the cathode is preferably composed exclusively of an NCM-based cathode active material containing 60 wt % or more of Ni.

The anode preferably includes a carbon (C)-based anode active material.

The carbon (C)-based anode active material may include at least one material selected from the group consisting of artificial graphite, natural graphite, graphitized carbon fiber, graphitized mesocarbon microbeads, fullerene, and amorphous carbon.

Meanwhile, each of the cathode and the anode is manufactured by mixing the corresponding active material with a conductive material, a binder, and a solvent to afford an electrode slurry, directly applying the electrode slurry on a current collector, and performing drying. Here, the current collector that is used may be aluminum (Al), but is not limited thereto. Since such a method of manufacturing the electrode is widely known in the art, a detailed description thereof will be omitted herein.

The binder serves to adhere active material particles to each other or to adhere active material particles to the current collector, and examples thereof may include, but are not limited to, polyvinyl alcohol, carboxymethyl cellulose, hydroxypropyl cellulose, diacetyl cellulose, polyvinyl chloride, carboxylated polyvinyl chloride, polyvinyl fluoride, ethylene-oxide-containing polymer, polyvinylpyrrolidone, polyurethane, polytetrafluoroethylene, polyvinylidene fluoride, polyethylene, polypropylene, styrene butadiene rubber, acrylated styrene butadiene rubber, epoxy resin, nylon, etc.

Also, the conductive material is used to impart conductivity to the electrode, and any material may be used, so long as it does not cause any chemical change in the configured battery and is electrically conductive. Examples thereof may include natural graphite, artificial graphite, carbon black, acetylene black, Ketjen black, carbon fiber, metal powder, metal fiber, and the like, in which the metal of the metal powder or the metal fiber is exemplified by copper, nickel, aluminum, silver, etc., and conductive materials such as polyphenylene derivatives, etc. may be used alone or in combinations of two or more thereof.

The separator inhibits a short circuit between the cathode and the anode and provides a passage for lithium ions to move. Examples of the separator may include those known in the art, including polyolefin-based polymer films, such as polypropylene, polyethylene, polyethylene/polypropylene, polyethylene/polypropylene/polyethylene, polypropylene/polyethylene/polypropylene, etc., multiple layers thereof, microporous films, woven fabrics, and nonwoven fabrics. Also, a film obtained by coating the porous polyolefin film with a resin having superior stability may be used.

A better understanding of the present disclosure may be obtained through the following Examples and Comparative Examples.

<Test 1> Test of Properties Depending on Type of Additive

In order to evaluate the high-temperature lifetime depending on the type of additive that is added to the electrolyte solution, the high-temperature lifetime was measured using additives of different types, as shown in Table 1 below. The results thereof are shown in Table 1 below and in FIG. 1.

In the preparation of the electrolyte solution, the lithium salt that was used was 0.5 M $LiPF_6$0.5LiFSI, and the solvent that was used was a solvent mixture comprising ethylene carbonate (EC), ethyl methyl carbonate (EMC) and diethyl carbonate (DEC), mixed at a weight ratio of 25:45:30.

The cathode that was used was NCM811, and the anode that was used was graphite.

Cut-off: 2.5-4.2 V.
C-rate: 1C
Temperature: high temperature of 45° C.

TABLE 1

| | Lithium salt (M) | | Solvent (weight ratio) | | | Additive (wt %) | | High-temperature lifetime (%) |
|---|---|---|---|---|---|---|---|---|
| | $LiPF_6$ | LiFSI | EC | EMC | DEC | VC | [$LiPO_2F_2$ Chemical Formula 1] | @50 cycles |
| Comparative Example 1 | 0.5 | 0.5 | 25 | 45 | 30 | 1.0 | — | — | 84.6 |
| Comparative Example 2 | 0.5 | 0.5 | 25 | 45 | 30 | 1.0 | 0.5 | — | 93.5 |
| Example 1 | 0.5 | 0.5 | 25 | 45 | 30 | 1.0 | — | 0.5 | 93.5 |

As is apparent from Table 1 and FIG. 1, the high-temperature lifetime was measured to be higher when 5-(4-cyanophenyl)-1-(4-fluorobenzyl)-1H-1,2,3-triazole-4-carbonitrile represented by Chemical Formula 1 was used along with VC as the additive (Example 1) compared to when VC was used alone as the additive (Comparative Example 1). Moreover, the high-temperature lifetime was equivalent to that of the case of using $LiPO_2F_2$ (Comparative Example 2). The additive VC may be typically used in an amount of 0.5 wt % to 3.0 wt % based on the weight of the electrolyte solution.

<Test 2> Test of Properties Depending on Weight Ratio of Anode Additive

In Test 2, in order to evaluate the high-temperature lifetime depending on the weight ratio of the additive of Chemical Formula 1, the high-temperature lifetime was measured using the additive of Chemical Formula 1 at the different weight ratios shown in Table 2 below. The results thereof are shown in Table 2 below and in FIG. 2.

In the preparation of the electrolyte solution, the lithium salt that was used was 0.5 M $LiPF_6$0.5LiFSI, and the solvent that was used was a solvent mixture comprising ethylene carbonate (EC), ethyl methyl carbonate (EMC) and diethyl carbonate (DEC), mixed at a weight ratio of 25:45:30.

The cathode that was used was NCM811, and the anode that was used was graphite.

Cut-off: 2.5-4.2 V
C-rate: 1C
Temperature: high temperature of 45° C.

TABLE 2

| | Lithium salt (M) | | Solvent (weight ratio) | | | Additive (wt %) | | | High-temperature lifetime (%) @50 cycles |
|---|---|---|---|---|---|---|---|---|---|
| | $LiPF_6$ | LiFSI | EC | EMC | DEC | VC | $LiPO_2F_2$ | [Chemical Formula 1] | |
| Comparative Example 1 | 0.5 | 0.5 | 25 | 45 | 30 | 1.0 | — | — | 84.6 |
| Comparative Example 2 | 0.5 | 0.5 | 25 | 45 | 30 | 1.0 | 0.5 | — | 93.5 |
| Example 1 | 0.5 | 0.5 | 25 | 45 | 30 | 1.0 | — | 0.5 | 93.5 |
| Example 2 | 0.5 | 0.5 | 25 | 45 | 30 | 1.0 | — | 1.0 | 94.2 |
| Example 3 | 0.5 | 0.5 | 25 | 45 | 30 | 1.0 | — | 1.5 | 91.5 |

As is apparent from Table 2 and FIG. 2, the high-temperature lifetime was increased when using the additive of Chemical Formula 1. Specifically, the high-temperature lifetime was the highest when the amount of the additive of Chemical Formula 1 was 1.0 wt % (Example 2), and was higher when the amount of the additive was 0.5 wt % (Example 1) than when the amount of the additive was 1.5 wt % (Example 3).

Although the preferred forms of the present disclosure have been disclosed for illustrative purposes with reference to the appended drawings, the present disclosure is not limited thereto, and is defined by the accompanying claims. Therefore, those skilled in the art will appreciate that various modifications, additions and substitutions are possible, without departing from the scope and spirit of the disclosure as disclosed in the accompanying claims.

What is claimed is:

1. An electrolyte solution for a lithium secondary battery, the electrolyte solution comprising:
   an electrolyte salt;
   an organic solvent; and
   an additive comprising 5-(4-cyanophenyl)-1-(4-fluorobenzyl)-1H-1,2,3-triazole-4-carbonitrile represented by Chemical Formula 1 below:

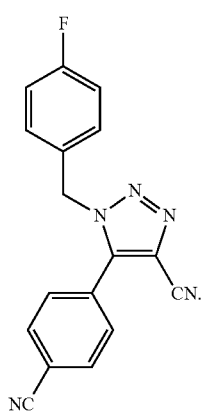

[Chemical Formula 1]

2. The electrolyte solution of claim 1, wherein an amount of the 5-(4-cyanophenyl)-1-(4-fluorobenzyl)-1H-1,2,3-triazole-4-carbonitrile is 1.5 wt % or less based on a total weight of the electrolyte solution.

3. The electrolyte solution of claim 1, wherein an amount of the 5-(4-cyanophenyl)-1-(4-fluorobenzyl)-1H-1,2,3-triazole-4-carbonitrile is 0.5 wt % to 1.0 wt % based on a total weight of the electrolyte solution.

4. The electrolyte solution of claim 1, wherein the additive further comprises vinyl chloride (VC) in an amount of 0.5 wt % to 3.0 wt % based on a total weight of the electrolyte solution.

5. The electrolyte solution of claim 1, wherein the electrolyte salt is any one compound or a mixture of two or more compounds selected from a group consisting of $LiPF_6$, $LiBF_4$, $LiClO_4$, LiCl, LiBr, LiI, $LiB_{10}Cl_{10}$, $LiCF_3SO_3$, $LiCF_3CO_2$, $LiAsF_6$, $LiSbF_6$, $LiAlCl_4$, $CH_3SO_3Li$, $CF_3SO_3Li$, $LiN(SO_2C_2F_5)_2$, $Li(CF_3SO_2)_2N$, $LiC_4F_9SO_3$, $LiB(C_6H_5)_4$, $Li(SO_2F)_2N(LiFSI)$, and $(CF_3SO_2)_2NLi$.

6. The electrolyte solution of claim 1, wherein the organic solvent is any one substance or a mixture of two or more substances selected from a group consisting of a carbonate-based solvent, an ester-based solvent, an ether-based solvent, and a ketone-based solvent.

7. A lithium secondary battery comprising an electrolyte solution, wherein the electrolyte solution comprises:
   an electrolyte salt;
   an organic solvent; and
   an additive comprising 5-(4-cyanophenyl)-1-(4-fluorobenzyl)-1H-1,2,3-triazole-4-carbonitrile represented by Chemical Formula 1 below:

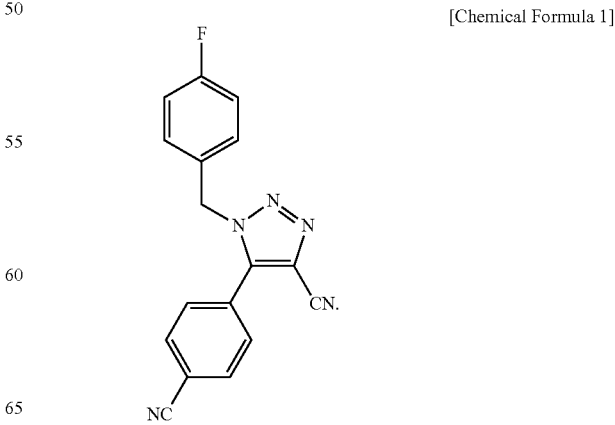

[Chemical Formula 1]

8. The lithium secondary battery of claim 7, further comprising:
- a cathode comprising a cathode active material containing Ni, Co and Mn;
- an anode comprising a carbon (C)-based anode active material; and
- a separator interposed between the cathode and the anode.

9. The lithium secondary battery of claim 8, wherein the lithium secondary battery is configured to exhibit a discharge retention of 84.6% or more after 50 cycles under conditions of a discharge end voltage of 2.5 V, a charge end voltage of 4.2 V, a temperature of 45° C. during charging and discharging, and a C-rate of 1C.

\* \* \* \* \*